(12) United States Patent
Kaar et al.

(10) Patent No.: US 8,931,476 B2
(45) Date of Patent: Jan. 13, 2015

(54) INHALER

(75) Inventors: Simon Kaar, Co. Cork (IE); Declan Walsh, Co. Kilkenny (IE); Derek Fenlon, Co. Wexford (IE); Dan Buck, Co. Waterford (IE)

(73) Assignee: IVAX Pharmaceuticals Ireland, Waterford (IE)

(*) Notice: Subject to any disclaimer, the term of this patent is extended or adjusted under 35 U.S.C. 154(b) by 404 days.

(21) Appl. No.: 13/377,037

(22) PCT Filed: Jun. 8, 2010

(86) PCT No.: PCT/EP2010/003426
§ 371 (c)(1),
(2), (4) Date: Mar. 22, 2012

(87) PCT Pub. No.: WO2010/142418
PCT Pub. Date: Dec. 16, 2010

(65) Prior Publication Data
US 2012/0174918 A1    Jul. 12, 2012

Related U.S. Application Data

(60) Provisional application No. 61/185,380, filed on Jun. 9, 2009.

(30) Foreign Application Priority Data

Jun. 18, 2009  (GB) .................................. 0910537.0

(51) Int. Cl.
*A61M 11/00*    (2006.01)
*A61M 15/00*    (2006.01)

(52) U.S. Cl.
CPC ......... *A61M 15/009* (2013.01); *A61M 15/0091* (2013.01); *A61M 15/0026* (2014.02)
USPC ............. 128/200.23; 128/200.12; 128/203.12

(58) Field of Classification Search
CPC .......... A61M 15/009; A61M 15/0065; A61M 15/0091
USPC ............. 128/200.23, 200.12, 200.14, 203.15, 128/203.21, 200.24, 203.12
See application file for complete search history.

(56) References Cited

U.S. PATENT DOCUMENTS 2,918,408 A    12/1959  Biel
3,948,264 A    4/1976   Wilke et al.
(Continued)

FOREIGN PATENT DOCUMENTS

CA    2494061 A1    2/2004
CA    2557168 A1    10/2005
(Continued)

OTHER PUBLICATIONS

International Search Report, dated Sep. 27, 2010, International Appl. No. PCT/EP2010/003426, filed Jun. 8, 2010, IVAX Pharmaceuticals Ireland.
(Continued)

*Primary Examiner* — Steven Douglas
(74) *Attorney, Agent, or Firm* — RatnerPrestia

(57) ABSTRACT

An inhaler, such as a breath-actuated metered-dose inhaler, for delivering medicament to a patient. The inhaler includes a housing for holding the medicament and having an air inlet and a medicament delivery port which together define an air flow path into which the medicament is dispensed. The air inlet includes an array of elongate apertures formed in the housing, the long sides of adjacent apertures facing each other. Each aperture is provided with a respective different opening in an outer surface of the housing. The opening of each aperture extends in two different planes such that, if at least a part of the opening is covered in one of the two different planes during inhalation by the patient, a void space is created between the cover and the aperture so as to provide an air flow path through the void space to the at least one aperture.

18 Claims, 2 Drawing Sheets

(56) References Cited

U.S. PATENT DOCUMENTS

| | | | |
|---|---|---|---|
| 5,685,294 A * | 11/1997 | Gupte et al. | 128/203.15 |
| D395,147 S | 6/1998 | Vidgrén et al. | |
| 5,904,139 A * | 5/1999 | Hauser | 128/200.23 |
| D441,859 S | 5/2001 | Pera | |
| 6,357,442 B1 * | 3/2002 | Casper et al. | 128/200.23 |
| 6,443,146 B1 * | 9/2002 | Voges | 128/200.14 |
| 6,994,083 B2 | 2/2006 | Foley et al. | |
| 7,051,731 B1 | 5/2006 | Rogerson | |
| 8,215,300 B2 * | 7/2012 | Steiner et al. | 128/203.15 |
| 8,534,281 B2 * | 9/2013 | Davies et al. | 128/203.15 |
| 8,616,195 B2 * | 12/2013 | Power et al. | 128/200.16 |
| 2004/0025867 A1 | 2/2004 | Holroyd | |
| 2005/0005933 A1 | 1/2005 | Seppala et al. | |
| 2006/0076010 A1 | 4/2006 | King | |
| 2006/0185672 A1 * | 8/2006 | Pinon et al. | 128/203.15 |
| 2006/0289005 A1 * | 12/2006 | Jones et al. | 128/203.15 |
| 2008/0142007 A1 * | 6/2008 | Fenlon | 128/203.15 |
| 2008/0196718 A1 | 8/2008 | Connell et al. | |
| 2010/0163042 A1 * | 7/2010 | Bhowmick et al. | 128/203.15 |

FOREIGN PATENT DOCUMENTS

| | | | |
|---|---|---|---|
| EP | 0561838 | | 9/1993 |
| EP | 0774986 | | 5/1997 |
| EP | 0966309 | | 12/1999 |
| EP | 1019126 | | 7/2000 |
| EP | 1294420 | | 3/2003 |
| EP | 1330280 | | 7/2003 |
| EP | 1386630 | A1 | 2/2004 |
| EP | 1486227 | | 12/2004 |
| EP | 1545634 | | 6/2005 |
| EP | 1667627 | | 6/2006 |
| EP | 2135199 | | 12/2009 |
| EP | 2178500 | | 4/2010 |
| EP | 2189176 | | 5/2010 |
| EP | 2314336 | | 4/2011 |
| EP | 2432530 | | 3/2012 |
| EP | 2436414 | | 4/2012 |
| EP | 2440271 | | 4/2012 |
| EP | 2459258 | | 6/2012 |
| EP | 2459259 | | 6/2012 |
| EP | 2459260 | | 6/2012 |
| EP | 2496294 | | 9/2012 |
| EP | 2502644 | | 10/2012 |
| EP | 2514462 | | 10/2012 |
| EP | 2514463 | | 10/2012 |
| EP | 2514464 | | 10/2012 |
| EP | 2514465 | | 10/2012 |
| EP | 2514466 | | 10/2012 |
| EP | 2514467 | | 10/2012 |
| EP | 2514468 | | 10/2012 |
| EP | 2596827 | | 5/2013 |
| EP | 2687253 | | 1/2014 |
| EP | 2705868 | | 3/2014 |
| GB | 2264238 | A1 | 8/1993 |
| GB | 2058630 | | 12/1996 |
| JP | 2006-502759 | | 2/2004 |
| JP | 2006-511297 | | 7/2004 |
| NZ | 240573 | | 5/1995 |
| WO | WO 01/04118 | A2 | 1/2001 |
| WO | WO 01/93933 | A2 | 12/2001 |
| WO | WO 0193933 | A2 | 12/2001 |
| WO | WO03/103563 | A2 | 12/2003 |
| WO | WO 2004/012801 | A1 | 2/2004 |
| WO | WO 2004/060260 | A2 | 7/2004 |
| WO | WO 2007/107160 | A1 | 9/2007 |
| WO | WO 2007/107160 | A1 | 9/2007 |
| WO | WO 2007/132217 | A1 | 11/2007 |
| WO | WO 2007/132217 | A1 | 11/2007 |
| WO | WO2010/142418 | | 12/2010 |

OTHER PUBLICATIONS

Japanese Office Action dated Jan. 31, 2014 corresponding to Japanese counterpart Patent Application No. 2012-514379.
European opposition dated Feb. 4, 2014 corresponding to European counterpart Patent Application 10727674.3.
European opposition dated Apr. 15, 2014 corresponding to European counterpart Patent Application 10727674.3.
Orion Corporation 2004 Annual Report (2004).
Instruction leaflet for Beclomet Easyhaler 200 microgram/dose inhalation powder (Feb. 2011).
Cemada, Adriana Munoz, Revista Cubana de Farmacia (2006).
Hirst, P.H. et al., Respiratory Medicine (2000) Band 95, 720-727.
Koskela, T. et al. Respiratory Medicine (2000) 94, 1229-1233.
Crystyn, Henry, Clin. Drug Invet. (2005), 26(4), 175-183.
Youtube.com/watch?v=uWkbkydzWpA, uploaded Sep. 24, 2008.
British Search Report, dated Oct. 13, 2009, corresponding to counterpart British Patent Application No. GB0910537.0.
Canadian Office Action, dated May 7, 2013, corresponding to counterpart Canadian Patent Application No. 2,760,647.
Chinese Office Action, dated Jan. 23, 2013, corresponding to counterpart Chinese Patent Application No. 201080025481.1.
Mexican Office Action, dated Jun. 14, 2014, corresponding to counterpart Mexican Patent Application No. MX/a/2011/012755.

* cited by examiner

INHALER

CROSS-REFERENCE TO RELATED APPLICATIONS

This application is the U.S. national phase application of PCT International Application No. PCT/EP2010/003426, filed Jun. 8, 2010, which claims priority to U.S. Provisional Patent Application No. 61/185,380, filed Jun. 9, 2009, and Great Britain Patent Application No. 0910537.0, filed Jun. 18, 2009, the contents of such applications being incorporated by reference herein.

FIELD OF THE INVENTION

This invention relates to an inhaler for delivering medication to a patient, and more particularly to a metered-dose inhaler.

BACKGROUND TO THE INVENTION

Inhalers for delivering medicament to a patient by inhalation are known. Such devices include metered-dose inhalers (of both pressurised and dry-powder types). Metered-dose inhalers typically comprise a medicament-containing vessel and an actuator housing having a medicament delivery outlet in the form of a mouthpiece or nosepiece.

The medicament-containing vessel may be a pressurized canister containing a mixture of active medicament and propellant. Such canisters are usually formed from a deep-drawn aluminium cup having a crimped lid which carries a metering valve assembly. The metering valve assembly is provided with a protruding valve stem which, in use, is inserted as a tight push fit into a so-called stem block in the actuator housing.

Metered-dose inhalers may either be of the manually operable type or the breath-actuated type. For the manually operable type, the patient self-administers the medicament by manually pressing the closed end of the canister into the actuator housing to cause movement of the canister relative to its valve stem (which is fixed in the stem block of the actuator housing). This movement is sufficient to actuate the metering valve assembly of the canister, resulting in the pressurised contents of a metering chamber being vented through the stem, through the stem block and its exit jet and orifice, and causing the medicament to exit the mouthpiece or nosepiece as an aerosol mist. Simultaneously with this action, the patient inhales through the nosepiece or mouthpiece, entraining the aerosol mist in the inhaled stream of air. The patient then releases the depression force on the canister which, under the action of an internal valve spring, moves upward with respect to the valve stem, returning to its resting position.

A more recent development is the so-called breath-actuated metered-dose inhaler, which serves to automatically displace the canister relative to its valve stem and release the contents of the canister's metering chamber in response to a patient's inspiration. The general purpose of such inhalers is to alleviate difficulties in coordinating actuation of the metering valve assembly with the patient's inspiration, and to provide for a maximal amount of medication to be drawn into the patient's lungs. A breath-actuated metered-dose inhaler is disclosed in WO 01/93933 A2.

The actuator housing is generally regarded as an integral part of the medicament delivery system, since the design of the housing can greatly affect the form of the medicament generated for inhalation by the patient. The actuator housing of a metered-dose inhaler typically includes an air inlet means for producing an air flow through the actuator housing into which the medicament is released.

Further, for breath-actuated inhalers, the air flow through the actuator housing typically operates or at least influences in some way the breath-actuated mechanism. Consequently, the actuator housing of such inhalers comprises air inlets designed to allow airflow through the housing. However, such air inlets exhibit the problem that they can be covered or occluded by the patient's hand or finger during use, thereby preventing or influencing the airflow through the actuator housing, with the result that the breath-actuated mechanism may malfunction. This problem is often exacerbated by the fact that the air inlets are provided on the actuator housing at positions which are convenient for handling the inhaler during use by the patient.

Thus, there is a need in the art to provide improved airflow configurations for inhalers that are less susceptible to being occluded or blocked by the patient during use, while at the same time allowing for convenient and comfortable operation by the patient.

SUMMARY OF THE INVENTION

According to the invention, there is provided an inhaler for delivering medicament to a patient, the inhaler comprising a housing for holding the medicament and having an air inlet means and a medicament delivery port which together define an air flow path into which the medicament is dispensed, wherein the air inlet means comprises an array of elongate apertures formed in the housing, the long sides of adjacent apertures facing each other, and each aperture being provided with a respective different opening in an outer surface of the housing, and wherein the opening of each aperture extends in two different planes such that, if at least a part of the opening is covered in one of the two different planes during inhalation by the patient, a void space is created between the cover and the aperture so as to provide an air flow path through the void space to the at least one aperture.

The inventors have found that the provision of multiple elongate apertures having respective different openings, each extending in two different planes, minimises the risk of the air inlet means becoming blocked. By different openings, it is meant that the opening of each aperture is defined, at least in part, by surfaces which are unique to that opening.

Embodiments of the invention may therefore prevent the air inlet means from being blocked by the patient during use, particularly by the patient's finger or thumb which each comprise soft tissue and can conform to different surface relief. By providing void spaces between the patient and the apertures when the patient covers the air inlet means, a substantial air flow path can be maintained which enables air to flow through the air inlet means despite the air inlet means being covered by the patient.

Embodiments may be particularly advantageous for use in conjunction with metered-dose inhalers, and particularly breath-actuated inhalers of this type containing a pressurised aerosol canister.

The invention may be applied to known inhalers with only minimal design changes, thereby reducing the potential for patient confusion, and avoiding large tooling costs that would be associated with more significant design changes.

The apertures of the air inlet means may be arranged to be parallel to one another. In this way, it may be possible to maximise the air flow through an air inlet means having a predetermined cross-sectional area. Raised, elongate formations having the form of ribs may be provided between adjacent apertures to define the different openings of the apertures.

The apertures may have a length in the range 2 mm to 20 mm, preferably in the range 4 mm to 12 mm. The apertures may have a width in the range 0.5 mm to 2 mm, preferably about 1 mm. The distance between adjacent apertures may be the same as the width of the apertures. The raised surface formations provided between adjacent apertures may have a height in the range 0.5 mm to 5 mm, preferably 1 mm to 3 mm.

In embodiments, each aperture is in effect provided in a respective different recess in the outer surface of the housing, which recess defines the opening of the aperture. The area of the opening of each aperture (in the outer surface of the housing) may be larger than an area of the aperture in the inner surface of the housing, for example the recess may surround the aperture. In general, however, it is preferred that at least one dimension of the recess is the same as, or similar to, the corresponding dimension of the aperture, in order to minimise the risk of the air inlet means becoming blocked.

As mentioned above, it is an essential feature of the invention that the opening of each aperture extends in two different planes, that is to say the opening defines some curvature or an edge between angled planes. In preferred embodiments, the opening of each aperture extends in different planes defining an angle of at least 45 degrees, and more preferably at least 60 degrees, and most preferably at least 80 degrees.

The housing may comprise an elongate body, which body may be unitary or multi-part. The air inlet means may conveniently be provided at an end of the elongate body opposite to an end at which the medicament delivery port is provided. In this case, the air inlet means may comprise a pair of the arrays of elongate apertures arranged at opposite sides of the end face of the elongate body, with a raised, elongate surface formation provided between the arrays.

The inhaler may be a metered-dose inhaler, particularly a breath-actuated metered-dose inhaler. The housing may be adapted for receiving a medicament-containing pressurised canister.

BRIEF DESCRIPTION OF THE DRAWINGS

An embodiment of the invention will now be described, by way of example only, with reference to the accompanying diagrams, in which.

DETAILED DESCRIPTION

The invention provides an inhaler, such as a breath-actuated pressurised metered-dose inhaler, for delivering medicament to a patient. The inhaler comprises a housing for holding the medicament, and having an air inlet means and a medicament delivery port which together define an air flow path into which the medicament is dispensed. The air inlet means comprises an array of elongate apertures formed in the housing, the long sides of adjacent apertures facing each other. Each aperture is provided with a respective different opening in an outer surface of the housing. The opening of each aperture extends in two different planes such that, if at least a part of the opening is covered in one of the two different planes during inhalation by the patient, a void space is created between the cover and the aperture so as to provide an air flow path through the void space to the at least one aperture.

Figure 1:
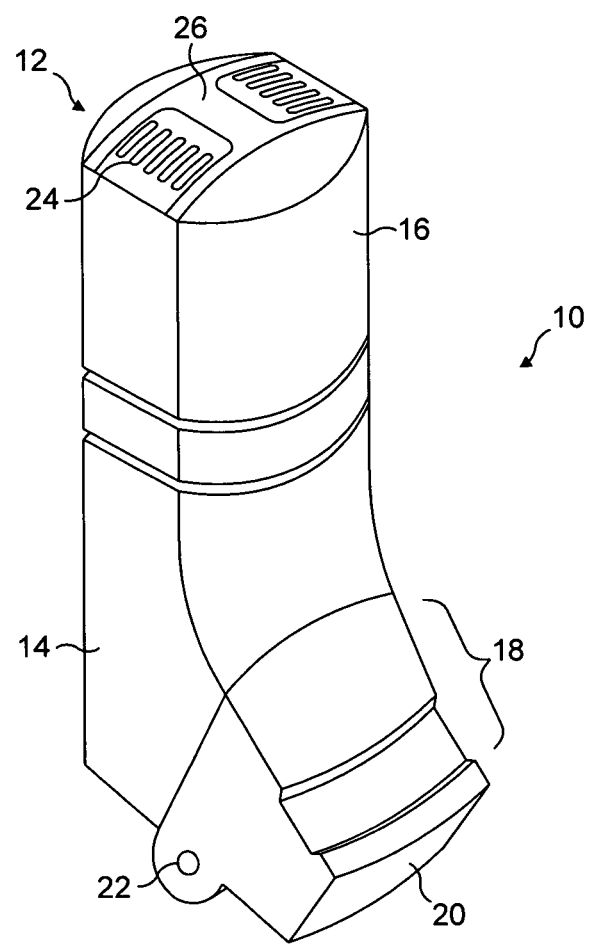
FIG. 1 shows an inhaler having an air inlet means according to the prior art document WO 01/93933 A2.

Referring to FIG. 1, there is shown a breath-actuated pressurised metered-dose inhaler 10 having an air inlet means 12 according to the prior art document WO 01/93933 A2 (the entire disclosure of which is incorporated herein by reference). A detailed explanation of the principle of operation of the inhaler 10 is not essential for understanding the invention, but a brief explanation will be provided by way of background information.

The inhaler 10 comprises a main body 14 and an end cap 16 which together define an elongate actuator housing. The main body 14, which is generally cylindrical in cross-section, is provided with a laterally extending mouthpiece 18 at one end and at the other end is adapted to receive a portion of a cylindrical medicament-containing pressurised canister. A stem block (not shown) is provided within the main body 14 for receiving the valve stem of the canister, and includes an exit jet and orifice communicating with the mouthpiece 18.

The end cap 16, which is also generally cylindrical in cross-section, is provided with the air inlet means 12 at one end and at the other end is adapted to receive the remaining portion of the canister. The main body 14 and end cap 16 are connected together by a threaded coupling. Components of the breath-actuated mechanism (not shown) are contained within both the main body 14 and the end cap 16.

The breath-actuated mechanism and canister contained within the housing 14,16 provide one or more air pathways such that air may pass from the air inlet means 12 to the mouthpiece 18 through the inside of the housing 14,16.

The mouthpiece 18 is provided with a dust cap 20 rotatable about an axis 22 between a first (closed) position (as shown in FIG. 1) and a second (open) position. In use, the patient rotates the dust cap 20 to its open position and inserts the exposed mouthpiece 18 into their mouth. On inhalation by the patient through the mouthpiece 18, a pressure differential in the housing 14,16 causes the breath-actuated mechanism to automatically displace the canister relative to its valve stem. Medicament contained within the metering chamber of the canister is accordingly released in response to the patient's inspiration.

During the patient's inspiration, air flows from the air inlet means 12, through the housing 14, 16, to the mouthpiece 18, and therefore to the patient. The medicament released from the metering chamber of the canister is entrained in this airflow.

After inhalation of the dose of medicament by the patient, the dust cap 22 is returned to its closed position, and this causes the breath-activated mechanism and the aerosol canister to reset to a rest position ready for subsequent use.

The air inlet means 12 of the inhaler 10 shown in FIG. 1 comprises a plurality of elongate apertures 24 formed in the end face of the end cap 16. The apertures 24 are arranged in a pair of arrays provided on opposite sides of the end face. Although there is a limited amount of three-dimensionality 26 provided between the arrays, the openings of adjacent apertures 24 in each of the arrays define a flat surface. Consequently, in use of the inhaler, it is a problem that the apertures 24 can become blocked by the finger or thumb of the patient, which may lead to a malfunction of the breath-actuated mechanism and/or incomplete or ineffective delivery of the medicament to the patient.

Figure 2:
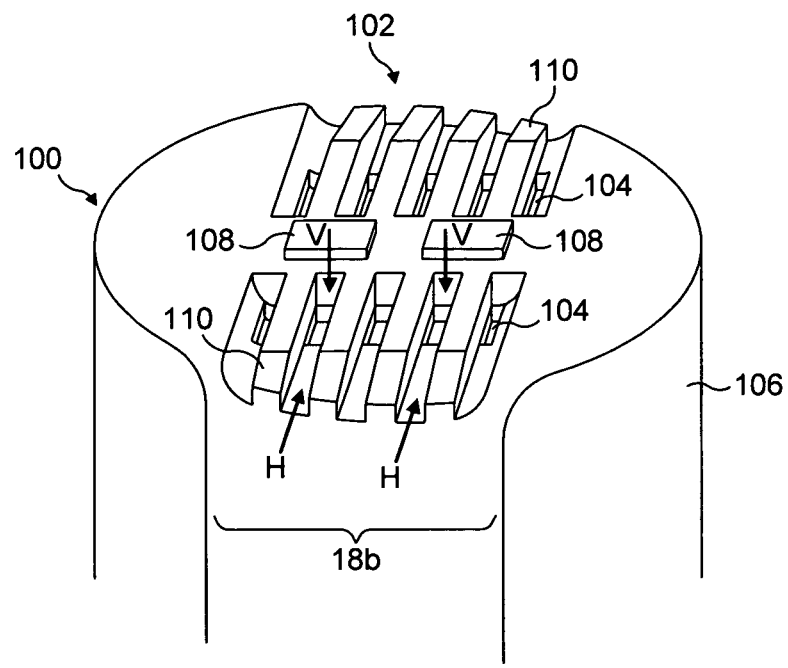
FIG. 2 is an enlarged view of an inhaler having an air inlet means according to an embodiment of the invention.
Figure 3:
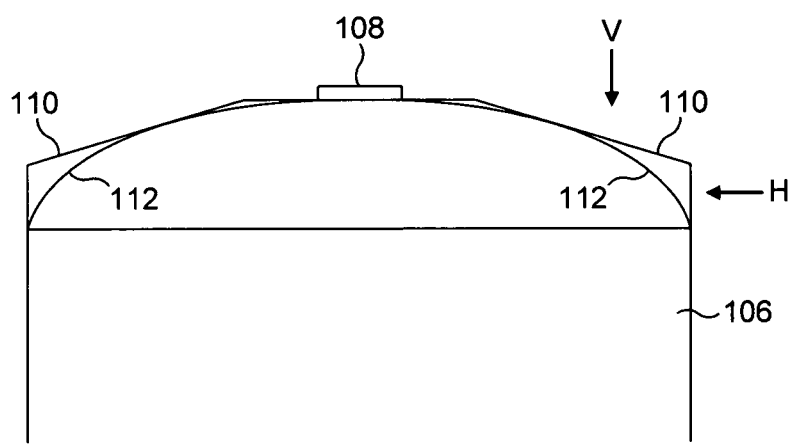
FIG. 3 is side view of the inhaler shown in FIG. 2.

Referring now to FIGS. 2 and 3, there is shown enlarged view of an inhaler 100 having an air inlet means 102 according to an embodiment of the invention. With the exception of its air inlet means 102, the inhaler 100 according to the invention has the same structure and use as the known inhaler 10 shown in FIG. 1. A detailed description of the individual components of the inhaler 100, other than the end cap having the air intake means 102, will accordingly be omitted. Similarly, a detailed description of the use of the inhaler 100 will also be omitted.

The air inlet means 102 of the inhaler 100 comprises a plurality of parallel, elongate apertures 104 having an approximately rectangular shape. The apertures 104 are formed in the end face of the end cap 106. The apertures 104 are arranged in two distinct arrays provided on opposite sides of the end face, each array comprising five apertures 104 whose long sides face one another. Short sides of the apertures 104 in one of the arrays face short sides of the apertures 104 in the other of the arrays, and are separated by a pair of elongate surface protrusions 108 which extend in a direction perpendicular to the length direction of the apertures 104.

Each of the apertures 104 is effectively recessed in the surface of the end cap 106, and the recess defines an opening of the aperture 104. The recesses are defined by raised, elongate surface protrusions in the form of moulded ribs 110 arranged between the long sides of adjacent apertures 104. Each recess is open at one end, with a corresponding end of each rib 110 being chamfered. As such, the opening of each aperture 104 extends in two substantially perpendicular planes: a horizontal plane corresponding to the "top" portion of the opening and a vertical plane corresponding to the "side" portion of the opening.

The apertures 104 have lengths which vary from 5 mm to 7 mm, and a width of 1 mm. A spacing between apertures 104 is 1.2 mm, and the elongate ribs 104 filling these spaces have a height of 2.5 mm.

In use of the inhaler 100, if the patient covers at least a part of the openings of the apertures 104 in one of the two different planes, for example with their finger or thumb, then void spaces are created between the patient and the apertures 104 so as to provide an air flow path through the void spaces to the apertures 104, thereby preventing the apertures 104 from being occluded or blocked by the patient.

In other words, if the air inlet means 102 is covered by a surface extending in the horizontal plane which prevents vertical air flow (as illustrated by the arrows labelled "V" in FIGS. 2 and 3) into the apertures 104, for example, the configuration of the air inlet means 102 is such that the openings of the apertures 104 extend at least partially in the vertical plane enabling horizontal air flow (as illustrated by the arrows labelled "H" in FIGS. 2 and 3) into the apertures 104. Conversely, if the air inlet means 102 is covered by a surface extending in the vertical plane which prevents horizontal air flow (as illustrated by the arrows labelled "H") into the apertures 104, the configuration of the air inlet means 102 is such the openings of the holes 24 extend in the horizontal to plane enabling vertical air flow (as illustrated by the arrows labelled "V") into the apertures 104.

With specific reference to FIG. 3, it can be seen that the elongate ribs 110 which define the openings of the apertures 104 stand proud of the surrounding surface 112 of the end cap 106. The elongate ribs 110 thus ensure a void space can be maintained between the patent's finger or thumb and the apertures 104.

A specific embodiment has been described herein for purpose of illustration. Various modifications will be apparent to a person skilled in the art and may be made without departing from the scope of the invention.

For example, although the embodiment described above is implemented as breath-actuated pressurised metered-dose inhaler, it will be understood that alternative embodiments may more generally comprise an inhaler for delivering medication to a patient by inhalation, wherein restriction or prevention of blockage of air inlets by the patient is desirable. Such prevention of blockage may, for example, be desirable in dry-powder inhalers in which a source of air is required for effective atomization of the medicament.

In the embodiment described above, the air inlet means is arranged in an end face of the end cap. In alternative embodiments the air inlet means may be provided elsewhere, such as in the end face of the main body, adjacent to the mouthpiece.

Components of an inhaler according to the invention will typically be moulded plastics components. Such components can conveniently be provided with the surface features of the invention.

In embodiments the inhaler comprises a medicament-containing pressurised canister containing a medicament and a propellant.

Typically, the medicament is selected from the group consisting of anti-inflammatory agents, anti-cholinergic agents, $\beta_2$-adrenoreceptor agonists, anti-infective agents, anti-histamines and combinations thereof.

Suitable anti-inflammatory agents include corticosteroids and NSAIDs. Suitable corticosteroids which may be used include those oral and inhaled corticosteroids and their prodrugs which have anti-inflammatory activity. Examples include methyl prednisolone, prednisolone, dexamethasone, fluticasone propionate, 6a,9a-difluoro-17a-[(2-furanylcarbonyl)oxy]-11-hydroxy-16a-methyl-3-oxo-androsta-1,4-diene-17-carbothioic acid S-fluoromethyl ester, 6a,9a-difluoro-11-hydroxy-16a-methyl-3-oxo-17a-propionyloxy-androsta-1,4-diene-17p-carbothioic acid S-(2-oxo-tetrahydro-furan-3S-yi) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6a,9c-difluoro-11-hydroxy-16a-methyl-17a-[(4-methyl-1,3-thiazole-5-carbonyl)oxy]-3-oxo-androsta-1,4-diene-17,8-carbothioic acid S-fluoromethyl ester and 6a,9a-difluoro-17a-[(2-furanylcarbonyl)oxy]-11-hydroxy-16a-methyl-3-oxo-androsta-1,4-diene-17-carbothioic acid S-fluoromethyl ester, more preferably 6a,9a-difluoro-17a-[(2-furanylcarbonyl)oxy]-11-hydroxy-16a-methyl-3-oxo-androsta-1,4-diene-17-carbothioic acid S-fluoromethyl ester.

Suitable NSAIDs include sodium chromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis, iNOS inhibitors, tryptase and elastase inhibitors, beta-2 integrin antagonists and adenosine receptor agonists or antagonists (e.g. adenosine 2a agonists), cytokine antagonists (e.g. chemokine antagonists) or inhibitors of cytokine synthesis.

Suitable other β2-adrenoreceptor agonists include salmeterol (e.g. as the xinofoate), salbutamol (e.g. as the sulphate or the free base), formoterol (e.g. as the fumarate), fenoterol or terbutaline and salts thereof.

Suitable anticholinergic agents are those compounds that act as antagonists at the muscarinic receptor, in particular those compounds, which are antagonists of the M1 and M2 receptors. Compounds include the alkaloid of the belladonna plants as illustrated by the likes of atropine, scopolamine, homatropine, hyoscyamine; these compounds are normally administered as a salt, being tertiary amines.

Particularly suitable anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-1,5-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118.

Suitable antihistamines (also referred to as H1-receptor antagonists) include any one or more of the numerous antagonists known which inhibit H1-receptors, and are safe for human use. All are reversible, competitive inhibitors of the interaction of histamine with H1-receptors. Examples include ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine. Exemplary antagonists are as follows:

Ethanolamines: carbinoxamine maleat, clemastine fumarate, diphenylhydramine hydrochloride, and dimenhydrinate.

Ethylenediamines: pyrilamine amleate, tripelennamine HCl, and tripelennamine citrate.

Alkylamines: chlorpheniramine and its salts such as the maleate salt, and acrivastine.

Piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutical acceptable salt.

Azelastine hydrochloride is yet another H1 receptor antagonist which may be used in combination with a PDE4 inhibitor.

Particularly suitable anti-histamines include methapyrilene and loratadine.

Preferably the medicament is presented in a formulation comprising a propellant and preferably a solvent; other preferred ingredients include surfactants, including oleic acid. Preferred solvents include ethanol, glycerols and glycols.

Preferred propellants include hydrofluoroalkanes; in particular 1,1,1,2-tetrafluoroethane (HFA134a); 1,1,1,2,3,3,3-Heptafluoropropane (HFA227); or combinations thereof. Preferably, the medicament is suspended in the propellant. Alternatively the medicament is dissolved in the propellant. The medicament may also be part suspended and part dissolved in the propellant.

EXAMPLES

The following medicament formulations were used in the inhaler:

Example Formulation 1

| Ingredient | Quantity/mg per ml |
| --- | --- |
| Beclomethasone dipropionate | 1.00 |
| Ethanol | 94.80 |
| HFA 134a | 1090.20 |

Example Formulation 2

| Ingredient | Mass/mg |
| --- | --- |
| Salbutamol sulphate | 0.1098 |
| HFA 134a | 27.8 |
| Ethanol | 3.6 |

The invention claimed is:

1. An inhaler for delivering medicament to a patient, the inhaler comprising a housing for holding the medicament and having an air inlet means and a medicament delivery port which together define an air flow path into which the medicament is dispensed,
wherein the air inlet means comprises an array of elongate apertures formed in the housing, wherein long sides of adjacent apertures face each other, and each aperture being provided with a respective different opening in an outer surface of the housing,
and wherein the opening of each aperture extends in two different planes such that, if at least a part of the opening is covered in one of two different planes during inhalation by the patient, a void space is created between a cover and the aperture so as to provide an air flow path through the void space to the at least one aperture, wherein a raised formation is provided in the outer surface of the housing between adjacent apertures to either limit or prevent a covered opening.

2. An inhaler according to claim 1, wherein the apertures are arranged to be parallel to one another.

3. An inhaler according to claim 1, wherein the raised formations are elongate raised formations.

4. An inhaler according to claim 1, wherein each aperture is provided in a respective different recess in the outer surface of the housing, which recess defines the opening of the aperture.

5. An inhaler according to claim 1, wherein the opening of each aperture extends in substantially perpendicular planes.

6. An inhaler according to claim 1, wherein the housing comprises an elongate body.

7. An inhaler according to claim 6, wherein the air inlet means is provided in an end face of the elongate body.

8. An inhaler according to claim 7, wherein the air inlet means comprises a pair of the arrays of elongate apertures arranged at opposite sides of the end face of the elongate body.

9. An inhaler according to claim 1, wherein the inhaler is a metered-dose inhaler.

10. An inhaler according to claim 1, wherein the inhaler is a breath-actuated metered-dose inhaler.

11. An inhaler according to claim 1, wherein the housing is adapted for receiving a medicament-containing pressurised canister.

12. An inhaler according to claim 11, wherein the inhaler comprises a medicament-containing pressurised canister containing a medicament and a propellant.

13. An inhaler according to claim 1, wherein the medicament is selected from the group consisting of anti-inflammatory agents, anti-cholinergic agents, $\beta_2$-adrenoreceptor agonists, anti-infective agents, anti-histamines and combinations thereof.

14. An inhaler according to claim 12, wherein said medicament is dissolved in said propellant or said medicament is suspended in said propellant.

15. An inhaler according to claim 1, wherein the medicament is selected from the group consisting of salbutamol, formoterol, salmeterol, fluticasone, budesonide, beclomethasone, tiotropium, ipratropium and combinations thereof.

16. An inhaler according to claim 7, wherein the medicament delivery port is arranged at an opposite end of the elongated body to the end face.

17. A metered-dose inhaler for delivering medicament to a patient, the inhaler comprising a housing for holding the medicament and having an air inlet means and a medicament delivery port which together define an air flow path into which the medicament is dispensed,
- wherein the housing comprises an elongate body and the air inlet means is provided in an end face of the elongate body,
- wherein the air inlet means comprises an array of elongate apertures formed in the housing, long sides of adjacent apertures facing each other, and each aperture being provided with a respective different opening in an outer surface of the housing,
- wherein each aperture is provided in a respective different recess in the outer surface of the housing, which recess defines the opening of the aperture,
- and wherein the opening of each aperture in the outer surface of the housing extends in two different planes defining an angle of at least 45 degrees to each other, such that, if at least a part of the opening is covered in one of the two different planes during inhalation by the patient, a void space is created between the patient and the aperture so as to provide an air flow path through the void space to the at least one aperture.

18. An inhaler according to claim 17, wherein the medicament delivery port is arranged at an opposite end of the elongate body to the end face.

* * * * *

UNITED STATES PATENT AND TRADEMARK OFFICE
CERTIFICATE OF CORRECTION

PATENT NO. : 8,931,476 B2
APPLICATION NO. : 13/377037
DATED : January 13, 2015
INVENTOR(S) : Simon Kaar et al.

It is certified that error appears in the above-identified patent and that said Letters Patent is hereby corrected as shown below:

In the Specification

At Column 2, line 50, "relief" should read --reliefs--

At Column 7, line 2, "CAS-1,5-63-9)" should read --CAS-115-63-9)--

Signed and Sealed this
Nineteenth Day of May, 2015

Michelle K. Lee
*Director of the United States Patent and Trademark Office*